US011753375B2

(12) United States Patent
Chadeayne

(10) Patent No.: US 11,753,375 B2
(45) Date of Patent: Sep. 12, 2023

(54) CRYSTALLINE PSILACETIN DERIVATIVES

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

(21) Appl. No.: 17/906,212

(22) PCT Filed: Mar. 18, 2021

(86) PCT No.: PCT/US2021/022942
§ 371 (c)(1),
(2) Date: Sep. 13, 2022

(87) PCT Pub. No.: WO2021/188782
PCT Pub. Date: Sep. 23, 2021

(65) Prior Publication Data
US 2023/0145648 A1    May 11, 2023

Related U.S. Application Data

(60) Provisional application No. 62/991,914, filed on Mar. 19, 2020.

(51) Int. Cl.
*C07D 209/16* (2006.01)
(52) U.S. Cl.
CPC ........ *C07D 209/16* (2013.01); *C07B 2200/13* (2013.01)
(58) Field of Classification Search
CPC .......................... C07D 209/16; C07D 2200/13
See application file for complete search history.

(56) References Cited

U.S. PATENT DOCUMENTS

| 2018/0221396 A1 | 8/2018 | Chadeayne |
| 2019/0105313 A1 | 4/2019 | Stamets |
| 2019/0142851 A1* | 5/2019 | Chadeayne ............ A61K 31/05 514/80 |
| 2019/0350949 A1 | 11/2019 | Kuecueksen et al. |
| 2020/0179349 A1 | 6/2020 | Yun et al. |

FOREIGN PATENT DOCUMENTS

WO    2019/099745 A1    5/2019

OTHER PUBLICATIONS

Byock, I. (2018). J. Palliat. Med. 21, 417-421.
Daniel, J. & Haberman, M. (2017). Mental Health Clinician, 7, 24-28.
Dolomanov, O. V., Bourhis, L. J., Gildea, R. J., Howard, J. A. K. & Puschmann, H. (2009). J. Appl. Cryst. 42, 339-341.
Feltman, R. (2019). Popular Science, https://popsci.com/story/health/psilocybin-magic-mushroom-fda-breakthroug?epression/.
Geiger, H. A., Wurst, M. G. & Daniels, R. N. (2018). ACS Chem. Neurosci. 9, 2438-2447.
Lehmann, S., Kieliba, T., Beike, J., Thevis, M. & Mercer-Chalmers-Bender, K. (2017). J. Chromatogr. B 1064,124-138.
Nichols, D. E. & Frescas, S. (1999). Synthesis, pp. 935-938.
Shelduck, G. M. (2015a). Acta Cryst. A71, 3-8.
Shelduck, G. M. (2015b). Acta Cryst. C71, 3-8.
Westrip, S. P. (2010). J. Appl. Cryst. 43, 920-925.
International Preliminary Report on Patentability dated Sep. 20, 2022, of PCT International Application No. PCT/US2021/022942, filed Mar. 18, 2021.
The Indole Shop viewed on the Wayback machine, captured Mar. 27, 2019. See substituted indoles then tryptamines. https://theindoleshop.com.
International Search Report and Written Opinion in International Application No. PCT/US2021/022942 dated May 12, 2021.
Li et al., "Synthesis and biological activity of novel 4-hydroxyl tryptamines", Journal of Molecular Science, 31(2), pp. 128-133, Apr. 2015.
Byrn et al., "Pharmaceutical Solids: A Strategic Approach to Regulatory Considerations", Pharma. Res., 12(7), pp. 945-954, 1995.
Caira, "Crystalline Polymorphism of Organic Compounds", Topics in Current Chemistry, 198, pp. 163-208, Jan. 1998.
Hilfiker et al., "Polymorphism in the Pharmaceutical Industry", Wile-VCH, 2006.
Brittain, "Polymorphism in Pharmaceutical Solids", Informa Healthcare, 2nd edition, 2009.
Kumar et al., "An overview of automated systems relevant in pharmaceutical salt screening", Drug Discovery Today, 12(23-24), pp. 1046-1053, Dec. 2007.
Serajuddin, "Salt formation to improve drug solubility", Advanced Drug Delivery Reviews, 59, pp. 603-616, May 2007.
Office Action in CA 3,169,783, dated May 8, 2023.
Stahl and Wermuth, "Handbook of Pharmaceutical Salts: Properties, Selection, and Use Part II 4. Classical Methods of Preparation of Polymorphs and Alternative Solid Forms", Verlag Helvetica Chimica Acta, Zürich, Switzerland, and Wiley-VCH, Weinheim, Germany, pp. 76-138, Apr. 2011.

* cited by examiner

*Primary Examiner* — Michael Barker
*Assistant Examiner* — Jed A Kucharczk
(74) *Attorney, Agent, or Firm* — RAPHAEL BELLUM PLLC

(57) ABSTRACT

The disclosure relates to crystalline psilacetin derivatives, compositions containing those crystalline derivatives, and methods of treatment using them. The crystalline psilacetin derivatives include crystalline 4-acetoxy-N-methyl-N-ethyl-tryptammonium (4-AcO-MET) hydrofumarate ("crystalline 4-AcO-MET hy-drofumarate"), crystalline 4-acetoxy-N-methyl-N-allyltryptammonium (4-AcO-MALT) hydrofumarate ("crystalline 4-AcO-MALT hydrofumarate"), and crystalline 4-acetoxy-N,N-diallyltryptammonium (4-AcO-DALT) fumarate fumaric acid ("crystalline 4-AcO-DALT fumarate fumaric acid").

18 Claims, 12 Drawing Sheets

CRYSTALLINE PSILACETIN DERIVATIVES

CROSS-REFERENCE TO RELATED APPLICATIONS

This application claims priority to U.S. Provisional Application No. 62/991,914 filed on Mar. 19, 2020, the disclosure of which is incorporated by reference.

TECHNICAL FIELD

This disclosure relates to crystalline psilacetin derivatives, to pharmaceutical compositions containing them and to methods of treatment/therapeutic uses of the crystalline psilacetin derivatives and the pharmaceutical compositions. The crystalline psilacetin derivatives according to the disclosure include crystalline 4-acetoxy-N-methyl-N-ethyltryptammonium (4-AcO-MET) hydrofumarate ("crystalline 4-AcO-MET hydrofumarate"), crystalline 4-acetoxy-N-methyl-N-allyltryptammonium (4-AcO-MALT) hydrofumarate ("crystalline 4-AcO-MALT hydrofumarate"), and crystalline 4-acetoxy-N,N-diallyltryptammonium (4-AcO-DALT) fumarate fumaric acid ("crystalline 4-AcO-DALT fumarate fumaric acid").

BACKGROUND

Psychotropic tryptamines have emerged as a leading candidate in the treatment of mood disorders, including anxiety, addiction, depression, and PTSD (Byock, 2018; Daniel & Haberman, 2017). Perhaps the best known of these tryptamines is psilocybin, which has recently been cleared for a number of clinical trials after receiving the "breakthrough therapy" designation from the U.S. Food and Drug Administration (Feltman, 2019). When psilocybin is consumed orally, it is hydrolysed to generate 4-hydroxy-N,N-dimethyltryptamine (4-HO-DMT), or psilocin, which is the active metabolite. Psilocin is a potent serotonin 2a agonist, which is the primary cause of its psychoactive properties (Geiger, et al. 2018).

Psilacetin, 4-acetoxy-N,N-dimethyltryptamine (4-AcO-DMT), is a synthetic alternative to psilocybin. It also acts as a prodrug of psilocin, with the acetyl group of psilacetin being hydrolysed as it is metabolized, converting 4-AcO-DMT to 4-HO-DMT. Psilacetin is easier to synthesize than psilocybin, and can also be produced at a lower cost, making it, perhaps, a better candidate for the delivery of psilocin (Nichols & Frescas, 1999).

4-acetoxy-substituted tryptamines should similarly function as prodrugs for the active metabolites of their psilocin analogues. Three such compounds are 4-acetoxy-N-methyl-N-ethyltryptamine (4-AcO-M ET), 4-acetoxy-N-methyl-Nallyltryptamine (4-AcO-MALT), and 4-acetoxy-N,N-diallyltryptamine (4-AcO-DALT). These are variations of psilacetin, which have garnered very little attention in the scientific literature, with only one reference being made to 4-AcO-MET in a chromatographic screening article (Lehmann, et al. 2017).

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to three crystalline psilacetin derivatives, specifically crystalline 4-acetoxy-N-methyl-N-ethyltryptammonium (4-AcO-MET) hydrofumarate ("crystalline 4-AcO-MET hydrofumarate"), crystalline 4-acetoxy-N-methyl-N-allyltryptammonium (4-AcO-MALT) hydrofumarate ("crystalline 4-AcO-MALT hydrofumarate"), and crystalline 4-acetoxy-N,N-diallyltryptammonium (4-AcO-DALT) fumarate fumaric acid ("crystalline 4-AcO-DALT fumarate fumaric acid").

In one embodiment, crystalline 4-AcO-MET hydrofumarate according to the disclosure is characterized by a monoclinic, $P2_1$ crystal system space group at a temperature of about 200 K; unit cell dimensions a=7.9555 (4) Å, b=13.3696 (7) Å, c=9.9708 (5) Å, and $\beta$=112.874 (2)°; or an XRPD having peaks at 11.7, 16.4, and 20.4°2θ±0.2°2θ.

In one embodiment, crystalline 4-AcO-MALT hydrofumarate according to the disclosure is characterized by a monoclinic, $P2_1$ crystal system space group at a temperature of about 297 K; unit cell dimensions a=7.9702 (4) Å, b=14.1788 (7) Å, c=9.8035 (5) Å, and $\beta$=113.394 (2)°; or an XRPD having peaks at 11.6, 15.9, and 17.5°2θ±0.2°2θ.

In one embodiment, crystalline 4-AcO-DALT fumarate fumaric acid according to the disclosure is characterized by a monoclinic, P2/c crystal system space group at a temperature of about 297 K; unit cell dimensions a=23.6642 (19) Å, b=8.4204 (18) Å, c=23.4002 (18) Å, and $\beta$=111.614 (6)°; or an XRPD having peaks at 9.1, 14.7, and 19.9°2θ±0.2°2θ.

The disclosure also relates to compositions comprising a crystalline psilacetin derivative according to the disclosure and to pharmaceutical compositions containing a crystalline psilacetin derivative according to the disclosure and an excipient.

The disclosure also relates to compositions comprising a combination of, as a first component, a crystalline psilacetin derivative according to the disclosure and a second component selected from (a) a serotonergic drug, (b) a purified psilocybin derivative, (c) one or two purified cannabinoids and (d) a purified terpene.

The disclosure further relates to methods of preventing or treating a physical and/or psychological disorders comprising the step of administering to a subject in need thereof an effective amount of a crystalline psilacetin derivative according to the disclosure and to pharmaceutical compositions containing a crystalline psilacetin derivative according to the disclosure, or a composition according to the disclosure.

The disclosure also relates to methods of preventing or treating inflammation and/or pain comprising the step of administering to a subject in need thereof an effective amount of a crystalline psilacetin derivative according to the disclosure and to pharmaceutical compositions containing a crystalline psilacetin derivative according to the disclosure, or a composition according to the disclosure.

DETAILED DESCRIPTION

Figure 1:
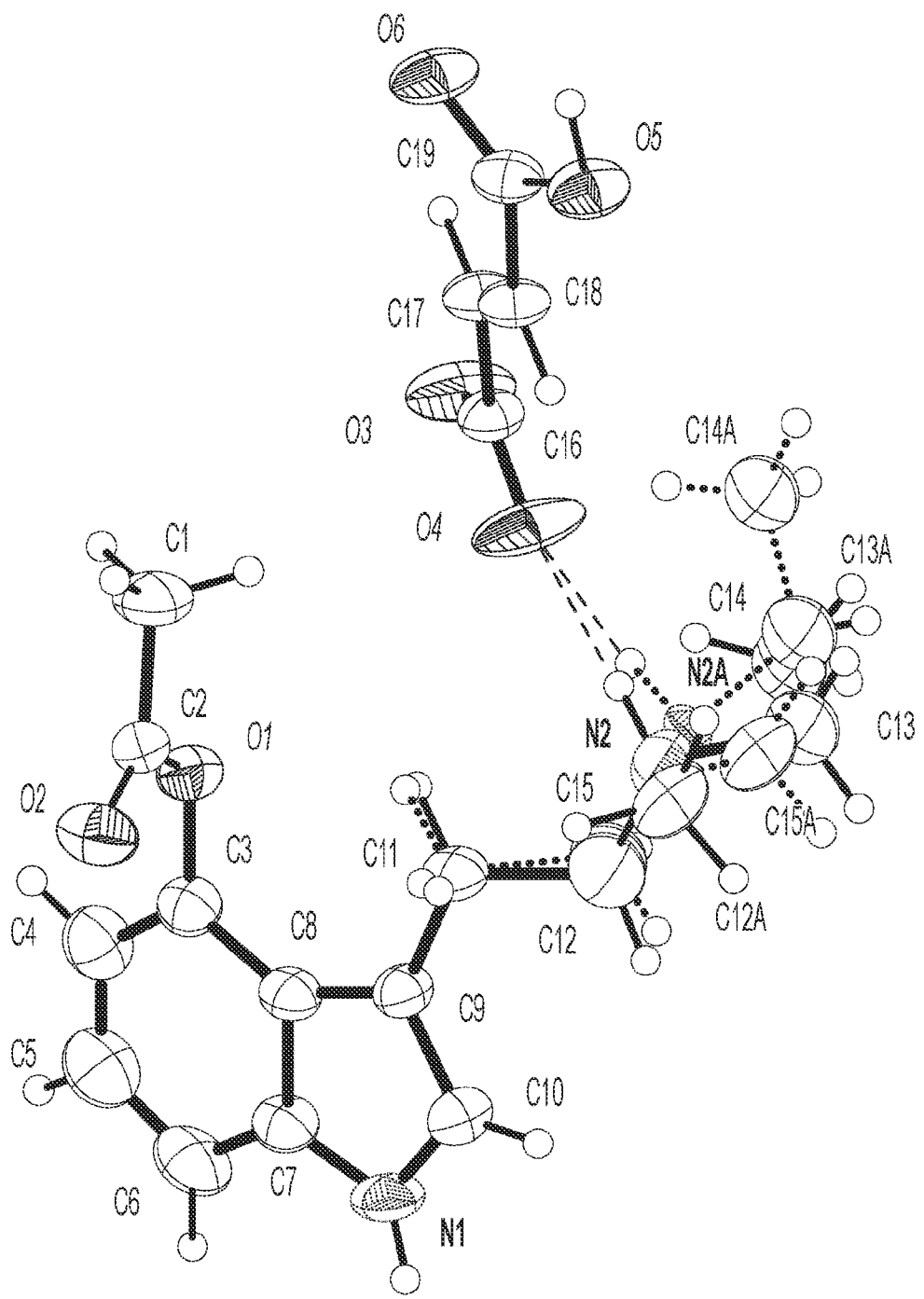
FIG. 1 shows the molecular structure of crystalline 4-AcO-MET hydrofumarate.

This disclosure relates to three crystalline psilacetin derivatives, specifically crystalline 4-acetoxy-N-methyl-N-ethyltryptammonium (4-AcO-MET) hydrofumarate ("crystalline 4-AcO-MET hydrofumarate"), crystalline 4-acetoxy-N-methyl-N-allyltryptammonium (4-AcO-MALT) hydrofumarate ("crystalline 4-AcO-MALT hydrofumarate"), and crystalline 4-acetoxy-N,N-diallyltryptammonium (4-AcO-DALT) fumarate fumaric acid ("crystalline 4-AcO-DALT fumarate fumaric acid"), and to pharmaceutical compositions containing a crystalline psilacetin derivative according to the disclosure. The therapeutic uses of a crystalline psilacetin derivative according to the disclosure, are described below as well as compositions containing them. The crystalline psilacetin derivatives according to the disclosure, and the methods used to characterize them are described below.

4-acetoxy-N-methyl-N-ethyltryptammonium (4-AcO-MET) hydrofumarate has the following structural formula:

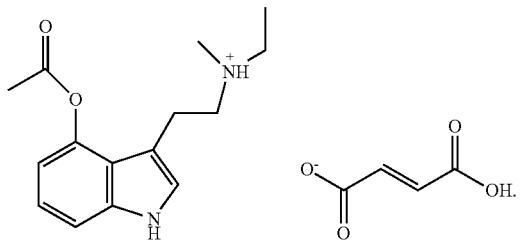 [SMILES: CCN(C)CCc1c[nH]c2cccc(OC(C)=O)c12 ; O=C([O-])/C=C/C(=O)O]

4-acetoxy-N-methyl-N-allyltryptammonium (4-AcO-MALT) hydrofumarate has the following structural formula:

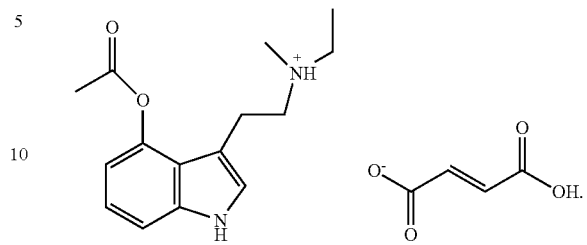

4-acetoxy-N,N-diallyltryptammonium (4-AcO-DALT) fumarate fumaric acid has the following structural formula:

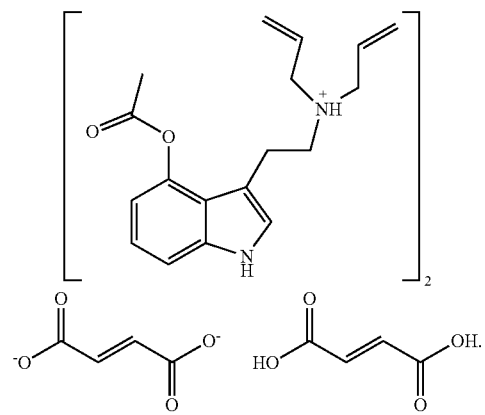

Methods of Treatment and Therapeutic Uses

In one embodiment, the crystalline psilacetin derivatives according to the disclosure, and the methods and the compositions—particularly the pharmaceutical compositions—of the disclosure are used to regulate the activity of a neurotransmitter receptor by administering a therapeutically effective dose of a crystalline psilacetin derivative of the disclosure. In another embodiment, a crystalline psilacetin derivative according to the disclosure, and the methods and the compositions—particularly the pharmaceutical compositions—of the disclosure are used to treat inflammation and/or pain by administering a therapeutically effective dose of a crystalline psilacetin derivative of the disclosure.

Methods of the disclosure administer a therapeutically effective amount of a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) to prevent or treat a disease or condition, such as those discussed below for a subject in need of treatment. A crystalline psilacetin derivative of the disclosure may be administered neat or as a composition comprising a crystalline psilacetin derivative of the disclosure as discussed below.

A crystalline psilacetin derivative of the disclosure may be used to prevent and/or treat a psychological disorder. The disclosure provides a method for preventing and/or treating a psychological disorder by administering to a subject in need thereof a therapeutically effective amount of a crystalline psilacetin derivative of the disclosure, including the preferred embodiments discussed herein. The psychological disorder may be chosen from depression; psychotic disorder;

schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

A crystalline psilacetin derivative of the disclosure may be used to prevent and/or treat a brain disorder. The disclosure provides a method for preventing and/or treating a brain disorder by administering to a subject in need thereof a therapeutically effective amount of a crystalline psilacetin derivative of the disclosure, including the preferred embodiments discussed above. The brain disorder is chosen from Huntington's disease, Alzheimer's disease, dementia, and Parkinson's disease.

A crystalline psilacetin derivative of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a crystalline psilacetin derivative of the disclosure, including the preferred embodiments discussed above.

A crystalline psilacetin derivative of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of a crystalline psilacetin derivative of the disclosure, including the preferred embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compositions

The disclosure also relates to compositions comprising an effective amount of a crystalline psilacetin derivative of the disclosure, especially pharmaceutical compositions comprising a therapeutically effective amount of a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) and a pharmaceutically acceptable carrier (also known as a pharmaceutically acceptable excipient). As discussed above, a crystalline psilacetin derivative of the disclosure may be, for example, therapeutically useful to prevent and/or treat the psychological and other disorders discussed above.

A composition or a pharmaceutical composition of the disclosure may be in any form which contains a crystalline psilacetin derivative of the disclosure. The composition may be, for example, a tablet, capsule, liquid suspension, injectable, topical, or transdermal. The compositions or pharmaceutical compositions generally contain, for example, about 1% to about 99% by weight of a crystalline psilacetin derivative of the disclosure and, for example, 99% to 1% by weight of at least one suitable pharmaceutical excipient. In one embodiment, the composition may be between about 5% and about 75% by weight of a crystalline psilacetin derivative of the disclosure with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) may be used as the "first purified psilocybin derivative" in the compositions described in US 2018/0221396 A1 and US 2019/0142851 A1. Accordingly, this disclosure provides a composition comprising as a first component: a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid); and as a second component selected from (a) a serotonergic drug, (b) a purified psilocybin derivative, (c) one or two purified cannabinoids and (d) a purified terpene; with the rest being at least one suitable pharmaceutical excipient or at least one other adjuvant, as discussed below. Such a composition may be a pharmaceutical composition wherein the components are present individually in therapeutically effective amounts or by combination in a therapeutically effective amount to treat a disease, disorder, or condition as described herein. A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Exemplary psilocybin derivatives include but are not limited to psilocybin itself and the psilocybin derivates described in paragraphs [0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments.

A pharmaceutical formulation of the disclosure may comprise, consist essentially of, or consist of (a) a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) and (b) a second active compound selected from a serotonergic drug, a purified psilocybin derivative, a purified cannabinoid, or a purified terpene and (c) a pharmaceutically acceptable excipient. The crystalline psilacetin derivative of the disclosure and the second active compound are each present in a therapeutically effective amount using a purposefully engineered and unnaturally occurring molar ratios. Exemplary molar ratios of the crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) to the second active compound in a composition of the disclosure include but are not limited to from about 0.1:100 to about 100:01, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing a crystalline psilacetin derivative as discussed above may be used in place of a "purified psilocybin derivative" in the compositions described in US 2018/0221396 A1 and US 2019/0142851 A1. Accordingly, the disclosure provides a pharmaceutical formulation comprising as (a) a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) and as a second component selected from (a) a purified psilocybin derivative, (b) one or two purified cannabinoids and (c) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in paragraphs [0245]-[0253] of US 2018/0221396 A1 and [0305]-[0311] US 2019/0142851 A1 as well as the disclosed preferred embodiments, incorporated here by reference. Some exemplary serotonergic drugs include the following molecules: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-l-methyl-C, 7-Methoxy-l-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-l-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-l-methyl-1,2,3,4-tetrahydro-C, alpha,N-Dimethyl-5-methoxy-T. For additional information regarding these compounds See Shulgin, A.T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof. In a preferred embodiment, the serotonergic drug is 3,4-methylenedioxymethamphetamine.

Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N, N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in paragraphs [0159] of US 2018/0221396 A1 and [0112]-[0160] US 2019/0142851 A1 as well as the disclosed preferred embodiments, incorporated here by reference. Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (Δ8-THC), Delta-8-tetrahydrocannabinolic acid (Δ8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-metha-no-2H-1-benzoxocin-5-methanol. In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in paragraphs [0160]-[0238] of US 2018/0221396 A1 and [0161]-[0300] US 2019/0142851 A1 as well as the disclosed preferred embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

Exemplary compositions of a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) and a second compound selected from a serotonergic drug, a purified psilocybin derivative, a purified cannabinoid, or a purified terpene in exemplary molar ratios are shown in Table 1.

TABLE 1

| Second Compound | Molar ratio of a crystalline psilacetin derivative:second compound | Molar ratio of a crystalline psilacetin derivative:second compound | Molar ratio of a crystalline psilacetin derivative:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |

TABLE 1-continued

| Second Compound | Molar ratio of a crystalline psilacetin derivative:second compound | Molar ratio of a crystalline psilacetin derivative:second compound | Molar ratio of a crystalline psilacetin derivative:second compound |
|---|---|---|---|
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

Exemplary pharmaceutical compositions of a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) and a second compound selected from a serotonergic drug, a purified psilocybin derivative, a purified cannabinoid, or a purified terpene and an excipient with exemplary molar ratios of a crystalline psilacetin derivative of the disclosure (e.g., crystalline 4-AcO-MET hydrofumarate, crystalline 4-AcO-MALT hydrofumarate, and/or crystalline 4-AcO-DALT fumarate fumaric acid) to the second compound are shown in Table 2.

TABLE 2

| Second Compound | Molar ratio of a crystalline psilacetin derivative:second compound | Molar ratio of a crystalline psilacetin derivative:second compound | Molar ratio of a crystalline psilacetin derivative:second compound |
|---|---|---|---|
| 3,4-methylenedioxymethamphetamine | About 1:100 to about 100:1 | About 1:25 to about 25:1 | About 1:5 to about 5:1 |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |

TABLE 2-continued

| Second Compound | Molar ratio of a crystalline psilacetin derivative:second compound | Molar ratio of a crystalline psilacetin derivative:second compound | Molar ratio of a crystalline psilacetin derivative:second compound |
|---|---|---|---|
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

An "effective amount" or a "therapeutically effective amount" of a crystalline psilacetin derivative according to the disclosure (e.g., crystalline 4-AcO-MET hydrofumarate, crystalline 4-AcO-MALT hydrofumarate, and/or crystalline 4-AcO-DALT fumarate fumaric acid) is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. A crystalline psilacetin derivative according to the disclosure, compositions and pharmaceutical compositions containing them may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the crystalline form of the psilacetin derivatives of the disclosure or produce undesirable biological effects or otherwise interact in a deleterious manner with any other component(s) of the pharmaceutical composition.

The compositions or pharmaceutical compositions of the disclosure may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, the crystalline form of the psilacetin derivatives of the disclosure may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of a crystalline psilacetin derivative of the disclosure in pure form, with a permeation enhancer, with stabilizers (e.g. antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

The preparation of crystalline 4-acetoxy-N-methyl-N-ethyltryptammonium (4-AcO-MET) hydrofumarate ("crystalline 4-AcO-MET hydrofumarate"), crystalline 4-acetoxy-N-methyl-N-allyltryptammonium (4-AcO-MALT) hydrofumarate ("crystalline 4-AcO-MALT hydrofumarate"), and crystalline 4-acetoxy-N,N-diallyltryptammonium (4-AcO-DALT) fumarate fumaric acid ("crystalline 4-AcO-DALT fumarate fumaric acid") are described below.

Synthesis and Crystallization

Single crystals of 4-acetoxy-N-methyl-N-ethyltryptammonium hydrofumarate suitable for X-ray analysis were obtained from the slow evaporation of an ethanolic solution of a commercial sample (The Indole Shop). A commercial sample of 4-acetoxy-N-methyl-N-allyltryptammonium hydrofumarate (The Indole Shop) was recrystallized by the slow evaporation of an aqueous solution to yield samples suitable for single crystal X-ray diffraction studies. Single crystals of bis(4-acetoxy-N,N-diallyltryptammonium) fumarate fumaric acid suitable for X-ray analysis were obtained from the slow evaporation of an acetone solution of a commercial sample (The Indole Shop).

Single crystal data, data collection, and structure refinement details are summarized in Table 3.

TABLE 3

|  | 4-AcO-MET Hydrofumarate | 4-AcO-MALT Hydrofumarate | 4-AcO-DALT Fumarate Fumaric Acid |
| --- | --- | --- | --- |
| Chemical formula | $C_{15}H_{21}N_2O_2 \cdot C_4H_3O_4$ | $C_{16}H_{21}N_2O_2 \cdot C_4H_3O_4$ | $C_2HO_2 \cdot C_{18}H_{23}N_2O_2 \cdot C_2H_2O_2$ |
| $M_r$ | 376.40 | 388.41 | 414.45 |
| Crystal system, space group | Monoclinic, $P2_1$ | Monoclinic, $P2_1$ | Monoclinic, $P2/c$ |
| Temperature (K) | 200 | 297 | 297 |
| a, b, c (Å) | 7.9555 (4), 13.3696 (7), 9.9708 (5) | 7.9702 (4), 14.1788 (7), 9.8035 (5) | 23.6642 (19), 8.4204 (18), 23.4002 (18) |
| β (°) | 112.874 (2) | 113.394 (2) | 111.614 (2) |
| V (Å$^3$) | 977.12 (9) | 1016.80 (9) | 4334.9 (6) |
| Z | 2 | 2 | 8 |
| Radiation type | Mo Kα | Mo Kα | Mo Kα |
| μ (mm$^{-1}$) | 0.10 | 0.09 | 0.09 |
| Crystal size (mm) | 0.24 × 0.2 × 0.2 | 0.34 × 0.24 × 0.2 | 0.22 × 0.2 × 0.12 |
| F(000) | 400 | 412 | 1760 |
| $D_x$ (Mg m$^{-3}$) | 1.279 | 1.269 | 1.270 |
| λ (Å) | 0.71073 | 0.71073 | 0.71073 |
| θ (°) | 2.7-25.4 | 2.7-25.6 | 2.6-24.9 |
| BLOCK | Colourless | Colourless | Colourless |
| Diffractometer | Bruker D8 Venture CMOS | Bruker D8 Venture CMOS | Bruker D8 Venture CMOS |
| Absorption correction | Absorption correction: multi-scan SADABS2016/2 (Bruker, 2016/2) was used for absorption correction. | Absorption correction: multi-scan SADABS2016/2 (Bruker, 2016/2) was used for absorption correction. | Absorption correction: multi-scan SADABS2016/2 (Bruker, 2016/2) was used for absorption correction. |

TABLE 3-continued

| | 4-AcO-MET Hydrofumarate | 4-AcO-MALT Hydrofumarate | 4-AcO-DALT Fumarate Fumaric Acid |
|---|---|---|---|
| | wR2(int) was 0.0597 before and 0.0530 after correction. The Ratio of minimum to maximum transmission is 0.9503. The λ/2 correction factor is Not present. | wR2(int) was 0.0631 before and 0.0557 after correction. The Ratio of minimum to maximum transmission is 0.9198. The λ/2 correction factor is Not present. | wR2(int) was 0.0596 before and 0.0507 after correction. The Ratio of minimum to maximum transmission is 0.9597. The λ/2 correction factor is Not present. |
| $T_{min}$, $T_{max}$ | 0.708, 0.745 | 0.686, 0.745 | 0.715, 0.745 |
| No. of measured, independent and observed [I > 2σ(I)] reflections | 21973, 3536, 3232 | 26393, 3797, 3516 | 99597, 4126, 3441 |
| $R_{int}$ | 0.036 | 0.039 | 0.040 |
| $\theta_{max}$, $\theta_{min}$ (°) | 25.4, 2.8 | 25.7, 2.8 | 25.8, 2.6 |
| h | −9→9 | −9→9 | −28→28 |
| k | −16→16 | −17→17 | −10→10 |
| l | −11→12 | −11→11 | −28→28 |
| Refinement | $F^2$ | $F^2$ | $F^2$ |
| Least-squares matrix | Full | Full | Full |
| $R[F^2 > 2\sigma(F^2)]$, $wR(F^2)$, S | 0.052, 0.146, 1.04 | 0.043, 0.113, 1.04 | 0.051, 0.140, 1.06 |
| No. of reflections | 3536 | 3797 | 4126 |
| No. of parameters | 271 | 264 | 354 |
| No. of restraints | 15 | 4 | 100 |
| Hydrogen site location | Mixed | Mixed | Mixed |
| H-atom treatment | H atoms treated by a mixture of independent and constrained refinement | H atoms treated by a mixture of independent and constrained refinement | H atoms treated by a mixture of independent and constrained refinement |
| w | $1/[\sigma^2(F_o^2) + (0.0865P)^2 + 0.4026P]$ where $P = (F_o^2 + 2F_c^2)/3$ | $1/[\sigma^2(F_o^2) + (0.0592P)^2 + 0.2448P]$ where $P = (F_o^2 + 2F_c^2)/3$ | $1/[\sigma^2(F_o^2) + (0.0627P)^2 + 3.2357P]$ where $P = (F_o^2 + 2F_c^2)/3$ |
| $(\Delta/\sigma)_{max}$ | <0.001 | <0.001 | <0.001 |
| $\Delta\rho_{max}$, $\Delta\rho_{min}$ (e Å$^{-3}$) | 0.39, −0.55 | 0.27, −0.16 | 0.51, −0.29 |
| Absolute Structure | Flack x determined using 1410 quotients [(I+) − (I−)]/[(I+) + (I−)] (Parsons, Flack and Wagner, Acta Cryst. B69 (2013) 249-259). | Flack x determined using 1577 quotients [(I+) − (I−)]/[(I+) + (I−)] (Parsons, Flack and Wagner, Acta Cryst. B69 (2013) 249-259). | |
| Absolute Structure Parameter | −0.3 (3) | 0.4 (3) | |
| Extinction Correction | | | SHELXL2018/3 (Sheldrick 2018), Fc* = kFc[1 + 0.001 × Fc$^2$λ$^3$/sin(2θ)]$^{-1/4}$ |
| Extinction Coefficient | | | 0.0057 (13) |

For all compounds, data collection: APEX3 (Bruker, 2018); cell refinement: SAINT (Bruker, 2018); data reduction: SAINT (Bruker, 2018). Program(s) used to solve structure: SHELXT2014 (Sheldrick 2015a) for umd1915b_a; SHELXT2014 (Sheldrick, 2015a) for umd1958i_a, umd1948g_a. For all compounds, program(s) used to refine structure: SHELXL2018 (Sheldrick, 2015b); molecular graphics: OLEX2 (Dolomanov et al., 2009); software used to prepare material for publication: publCIF (Westrip, 2010).

The molecular structure of crystalline 4-AcO-MET hydrofumarate is shown in FIG. 1. Hydrogen bonds are shown as dashed lines. The asymmetric unit contains one 4-acetoxy-N-methyl-N-ethyltryptammonium ($C_{15}H_{21}N_2O_2^+$) cation and one hydrofumarate ($C_4H_3O_2$) anion. The indole ring system of the compound is near planar with a r.m.s. deviation from planarity of 0.015 Å. The hydrofumarate anion is slightly twisted, demonstrating a deviation from planarity of 0.158 Å, and a carboxylate to carboxylic acid plane normal angle of 23.0 (3)°. The N-methyl-N-ethyl group is disordered over two orientations with a 0.760 (7):0.24 (7) ratio. The carboxylate group of the hydrofumarate appears to have localized single and double bonds, with C—O distances of 1.209 (5) Å and 1.267 (4) Å.

Figure 2:
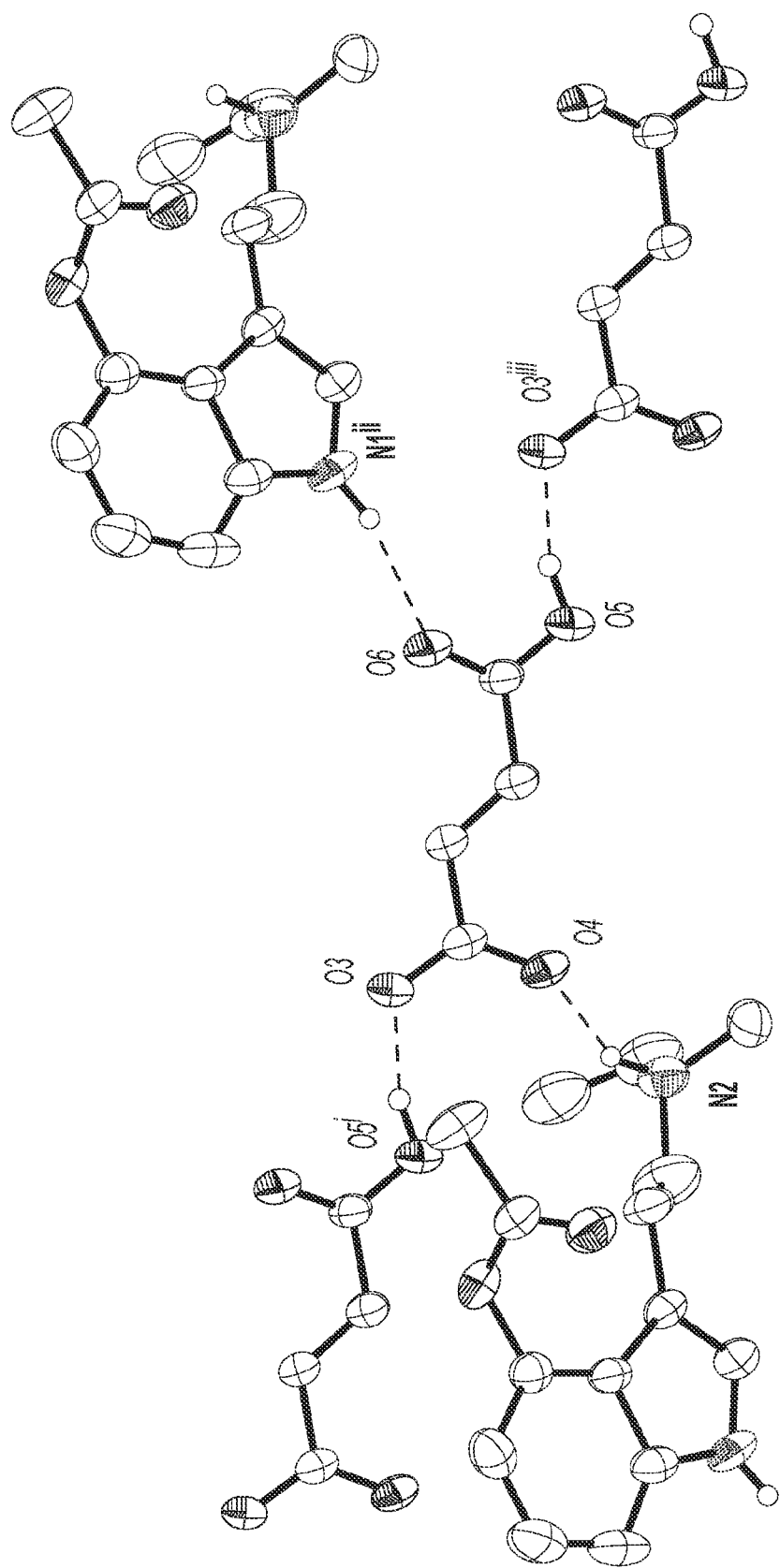
FIG. 2 shows the hydrogen bonding of crystalline 4-AcO-MET hydrofumarate.

In the extended structure of 4-AcO-MET hydrofumarate, the N-methyl-N-ethyltryptammonium cations and hydrofumarate anions are linked together in a two-dimensional network along the (010) plane through N—H⋯O and O—H⋯O hydrogen bonds. The O—H of the hydrofumarate hydrogen bonds with the carbonyl oxygen of the carboxylate unit of another hydrofumarate ion, the ammonium N—H hydrogen bonds to the negatively charged oxygen of the carboxylate group of a hydrofumarate ion, and the indole N—H hydrogen bonds to the carbonyl oxygen of the carboxylic acid unit of a hydrofumarate ion, as shown in FIG. 2.

Figure 3:
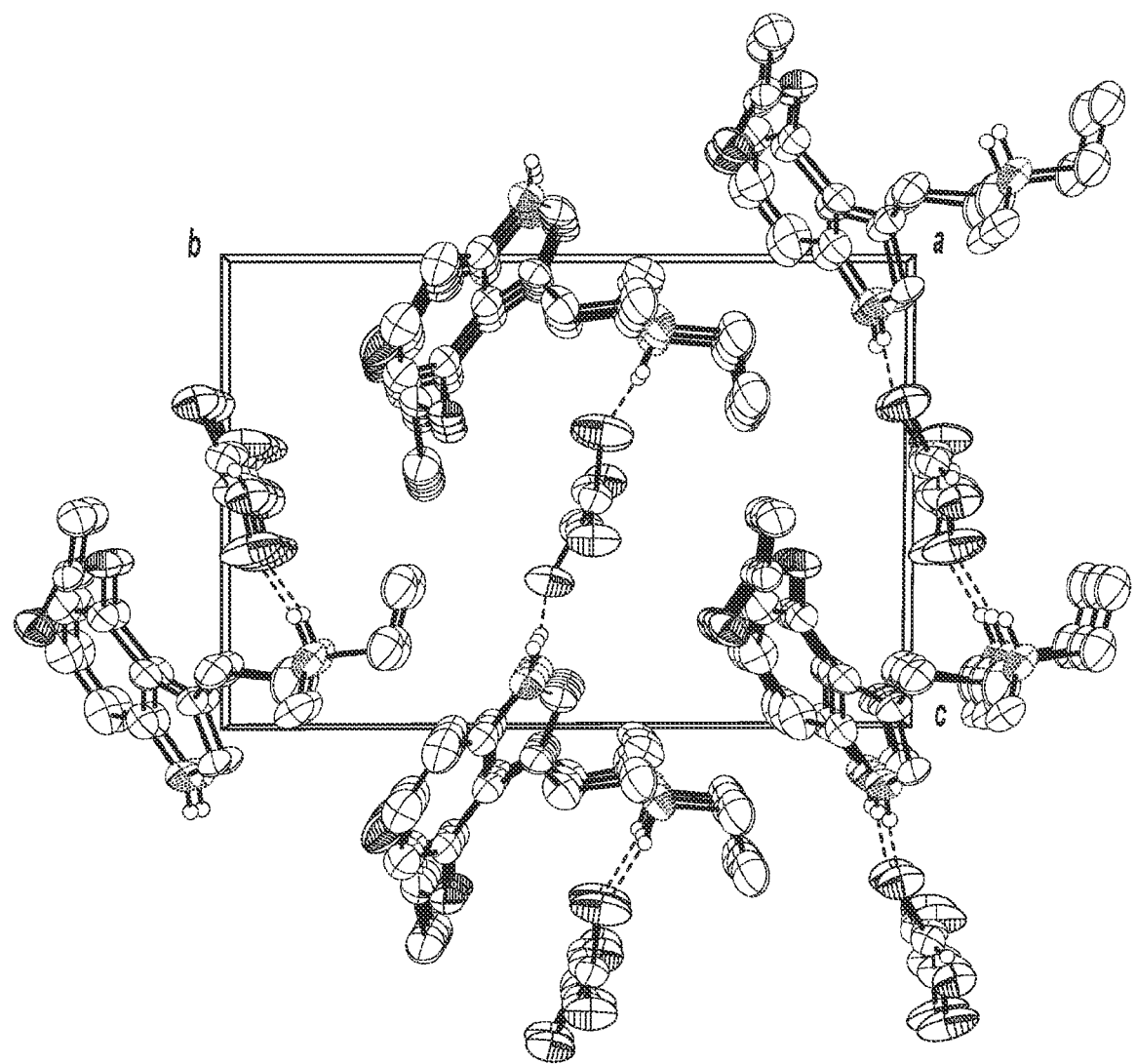
FIG. 3 shows the crystal packing of crystalline 4-AcO-MET hydrofumarate.

The crystal packing of 4-AcO-MET hydrofumarate viewed along the a-axis is shown in FIG. 3.

Figure 4:
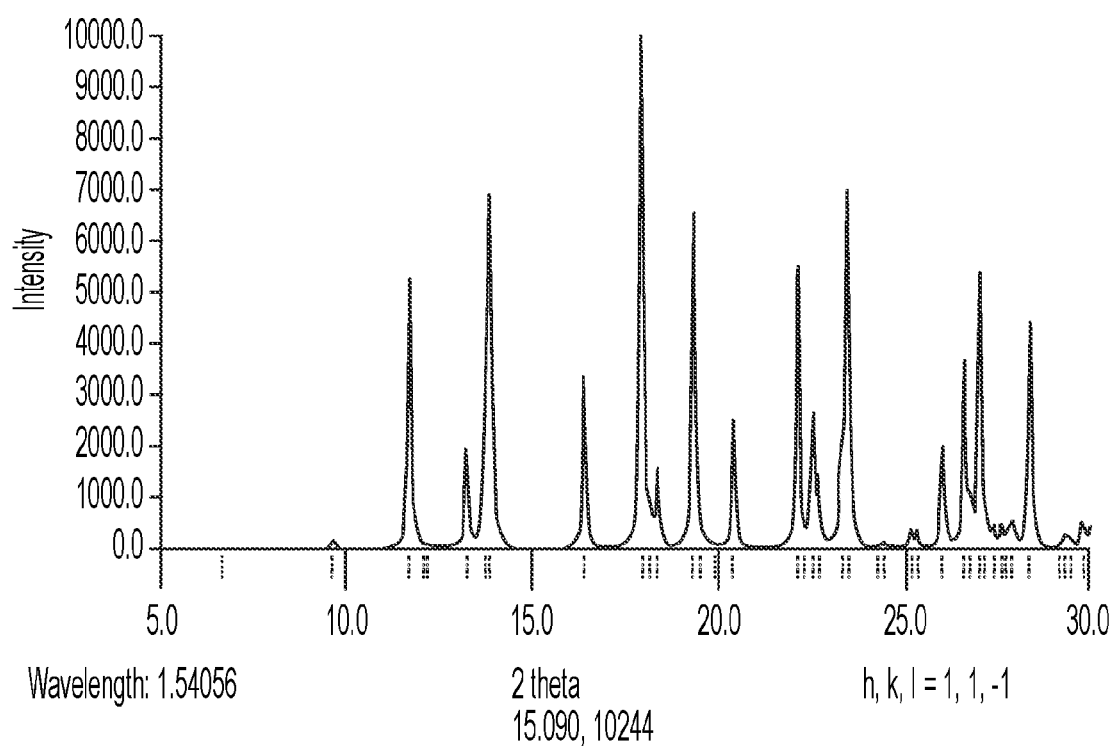
FIG. 4 shows a simulated x-ray power diffraction (XRPD) of crystalline 4-AcO-MET hydrofumarate.

FIG. 4 is a simulated x-ray powder diffraction (XRPD) of crystalline 4-AcO-MET hydrofumarate from its single crystal data. Crystalline 4-AcO-MET hydrofumarate may be characterized by the XRPD peaks at 11.7, 16.4, and 20.4°2θ±0.2°2θ as well as by an XRPD pattern substantially similar to FIG. 4.

Figure 5:
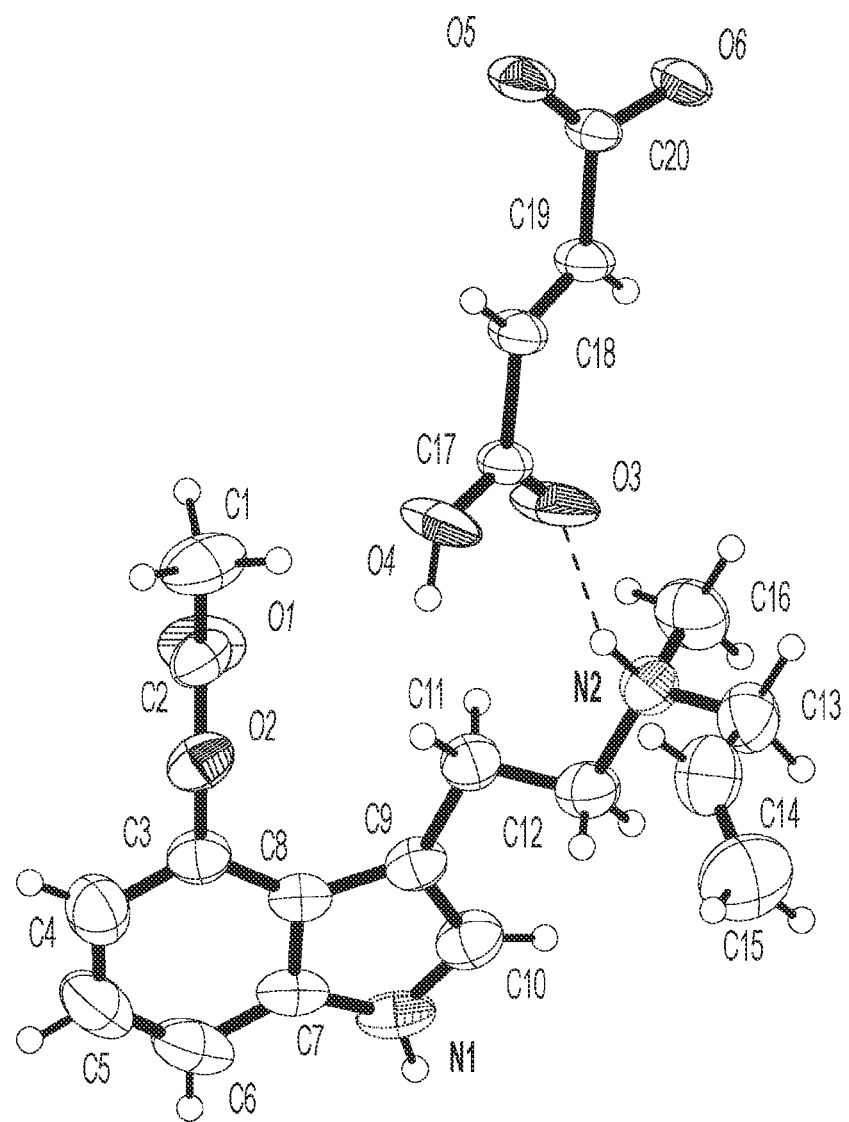
FIG. 5 shows the molecular structure of crystalline 4-AcO-MALT hydrofumarate.

The molecular structure of crystalline 4-AcO-MALT hydrofumarate is shown in FIG. 5. Hydrogen bonds are shown as dashed lines. The asymmetric unit contains one 4-acetoxy-N-methyl-N-allyltryptammonium ($C_{16}H_{21}N_2O_2^+$) cation and one hydrofumarate ($C_4H_3O_2^-$) anion. The indole ring system of the compound is near planar with a r.m.s. deviation from planarity of 0.006 Å. The hydrofumarate anion is slightly twisted, showing a deviation from planarity of 0.128 Å, and a carboxylate to carboxylic acid twist of 18.6 (2)°. The carboxylate group of the hydrofumarate appears to have localized single and double bonds, with C—O distances of 1.216 (3) Å and 1.291 (4) Å.

Figure 6:
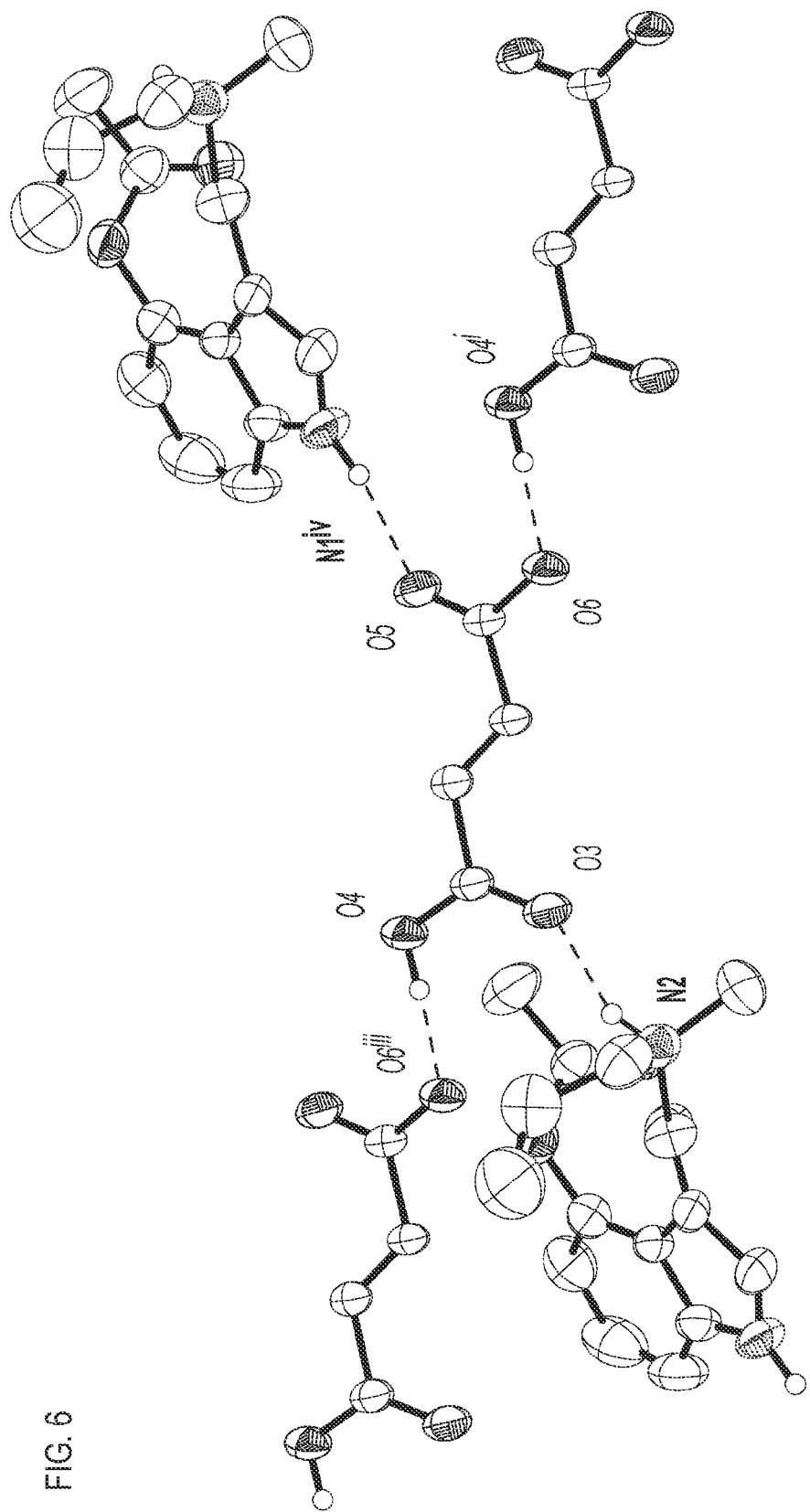
FIG. 6 shows the hydrogen bonding of crystalline 4-AcO-MALT hydrofumarate.

In the extended structure of 4-AcO-MALT hydrofumarate, the N-methyl-N-allyltryptammonium cations and hydrofumarate anions are linked together in an infinite two-dimensional network along (010) through N—H···O and O—H···O hydrogen bonds. The O—H of the hydrofumarate hydrogen bonds with the negatively charged oxygen of the carboxylate unit of another hydrofumarate ion, the indole N—H hydrogen bond to the carbonyl oxygen of the carboxylate group of the hydrofumarate ion, and the ammonium N—H hydrogen bonds to the carbonyl oxygen of the carboxylic acid unit of the hydrofumarate ion, as shown in FIG. 6.

Figure 7:
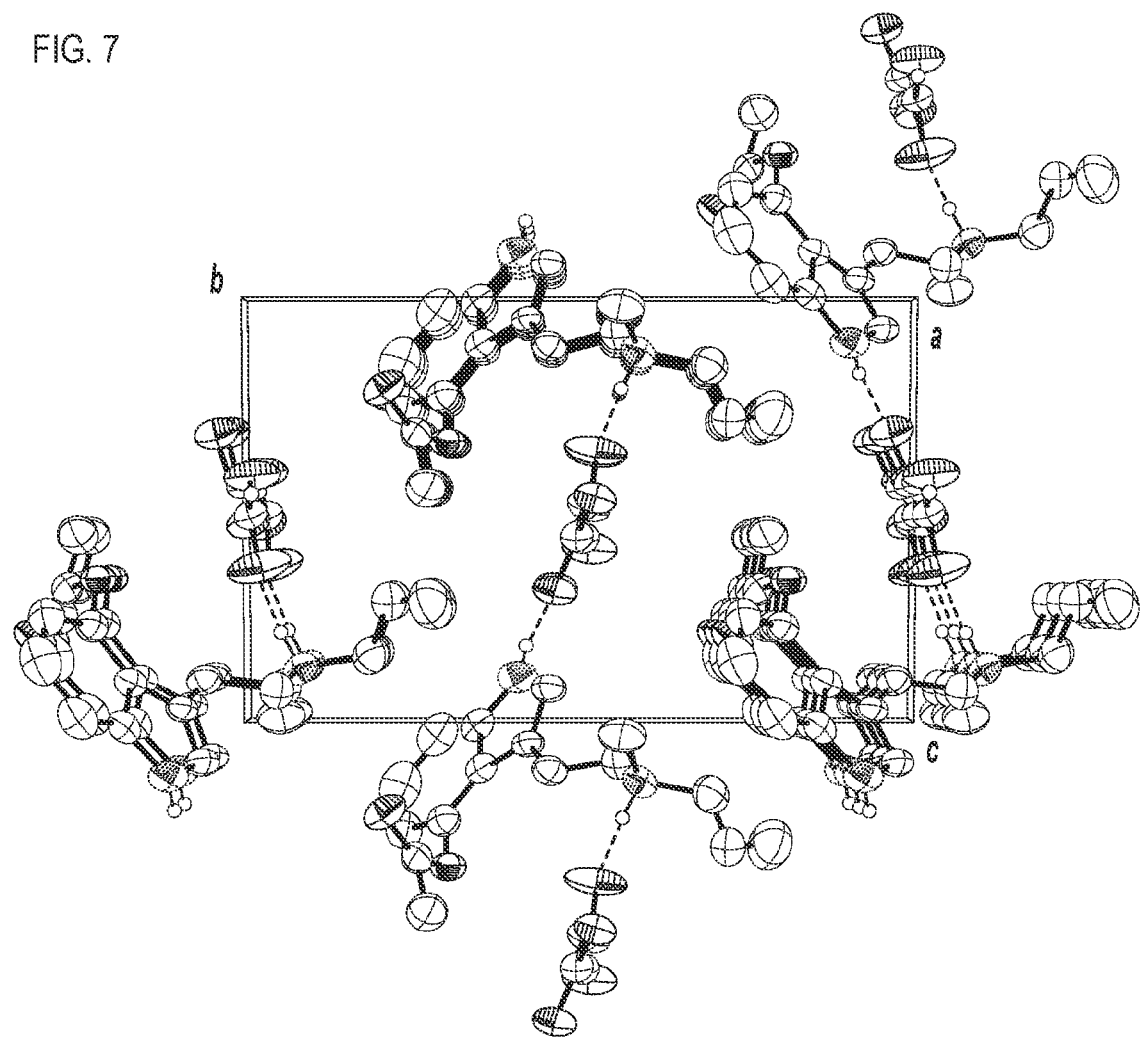
FIG. 7 shows the crystal packing of crystalline 4-AcO-MALT hydrofumarate.

The crystal packing of 4-AcO-MALT hydrofumarate viewed along the a-axis is shown in FIG. 7.

Figure 8:
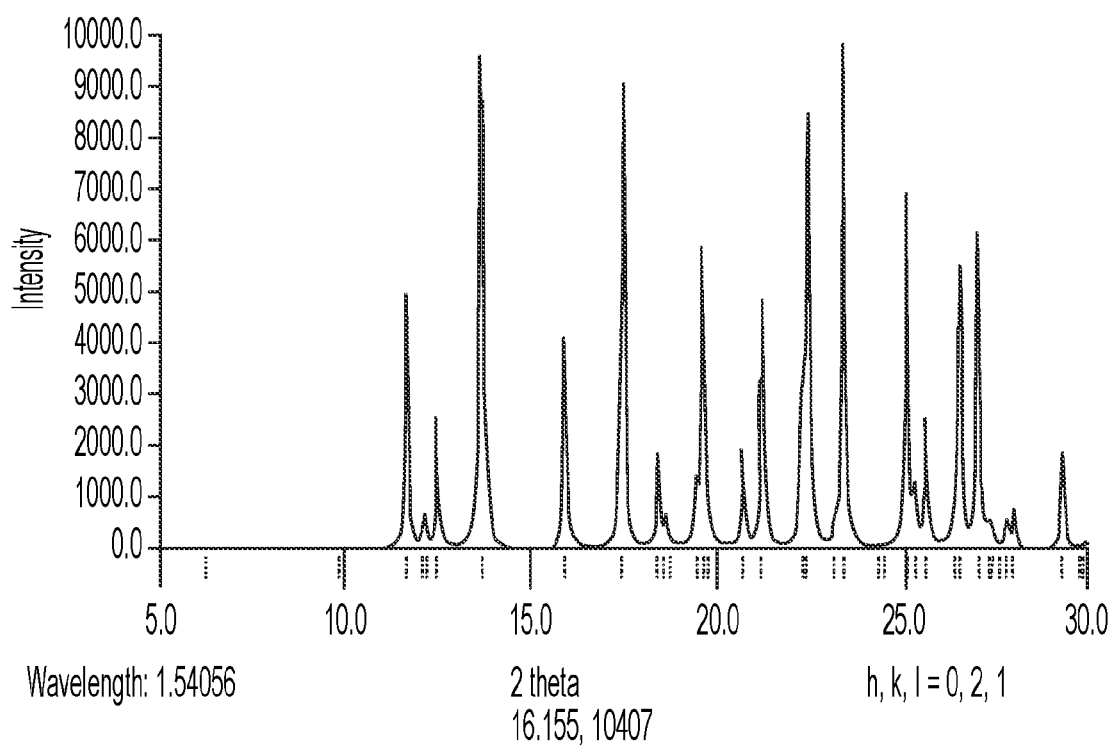
FIG. 8 shows a simulated x-ray power diffraction (XRPD) of crystalline 4-AcO-MALT hydrofumarate.

FIG. 8 is a simulated x-ray powder diffraction (XRPD) of crystalline 4-AcO-MALT hydrofumarate from its single crystal data. Crystalline 4-AcO-MALT hydrofumarate may be characterized by the XRPD peaks at 11.6, 15.9, and 17.5°2θ±0.2°2θ as well as by an XRPD pattern substantially similar to FIG. 8.

Figure 9:
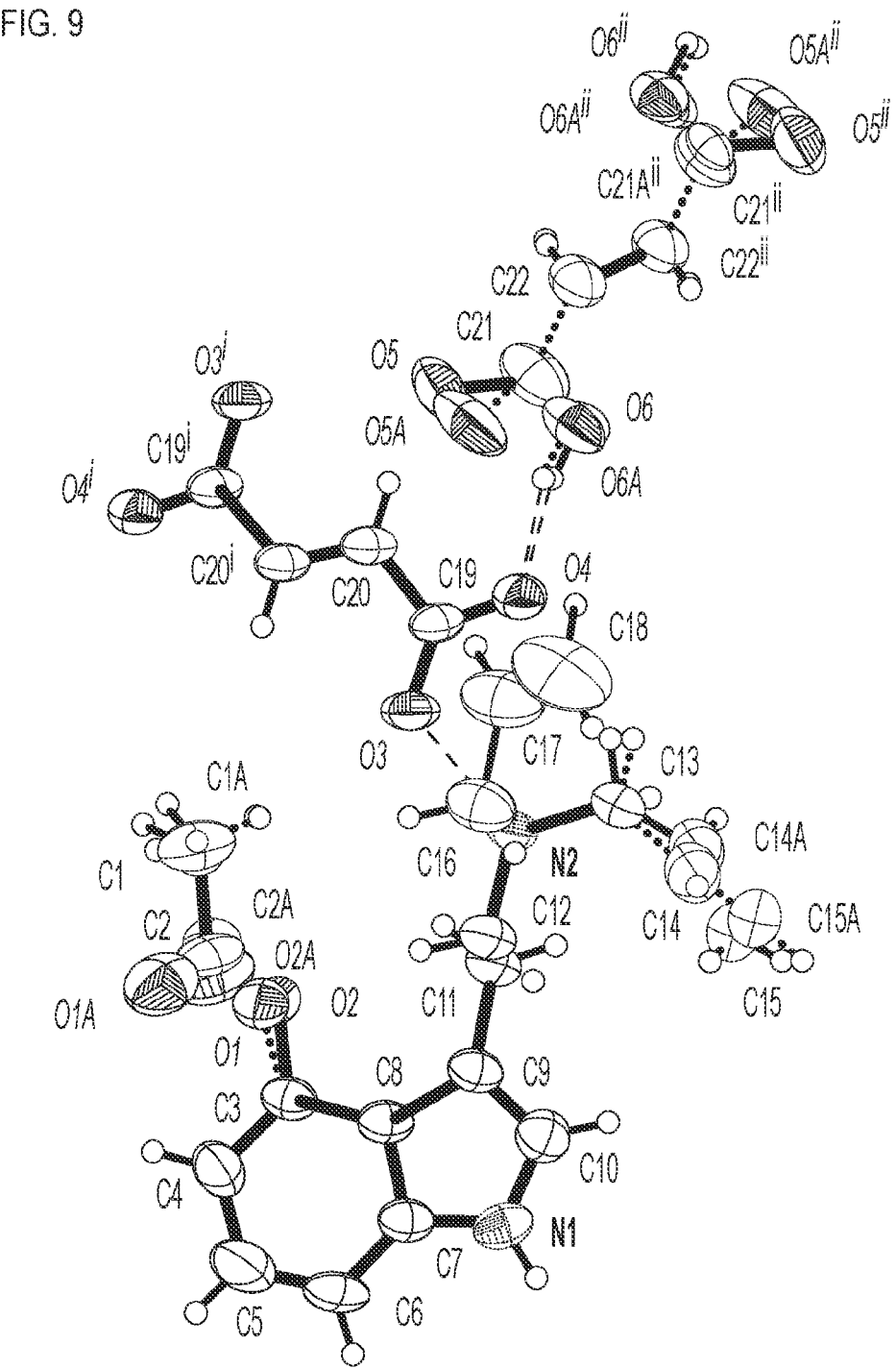
FIG. 9 shows the molecular structure of crystalline 4-AcO-DALT fumarate fumaric acid.

The molecular structure of crystalline 4-AcO-DALT fumarate fumaric acid is shown in FIG. 9. Hydrogen bonds are shown as dashed lines. The asymmetric unit contains one 4-acetoxy-N,N-diallyltryptammonium ($C_{18}H_{23}N_2O_2^+$) cation, one half of a fumarate ($C_2HO_2^-$) dianion, and one half of a fumaric acid ($C_2H_2O_2$) molecule. The indole ring system of the compound is near planar with a r.m.s. deviation from planarity of 0.016 Å. The full fumarate dianion is generated through inversion, and also shows great planarity, with a r.m.s. deviation from planarity of only 0.004 Å. The full disordered fumaric acid molecule is generated through inversion, and also demonstrates planarity, with r.m.s. deviations from planarity of 0.082 Å and 0.083 Å for the two configurations. One of the two allyl groups in the molecule is disordered over two orientations with a 0.904 (4):0.096 (4) ratio. The fumaric acid molecule is also disordered over two components with a 0.52 (4):0.48 (4) ratio. The 4-acetoxy group also shows a disorder over two orientations with a 0.62 (4):0.38 (4) ratio. The carboxylate group of the fumarate is delocalized, with C—O distances of 1.251 (3) Å and 1.258 (2) Å.

Figure 10:
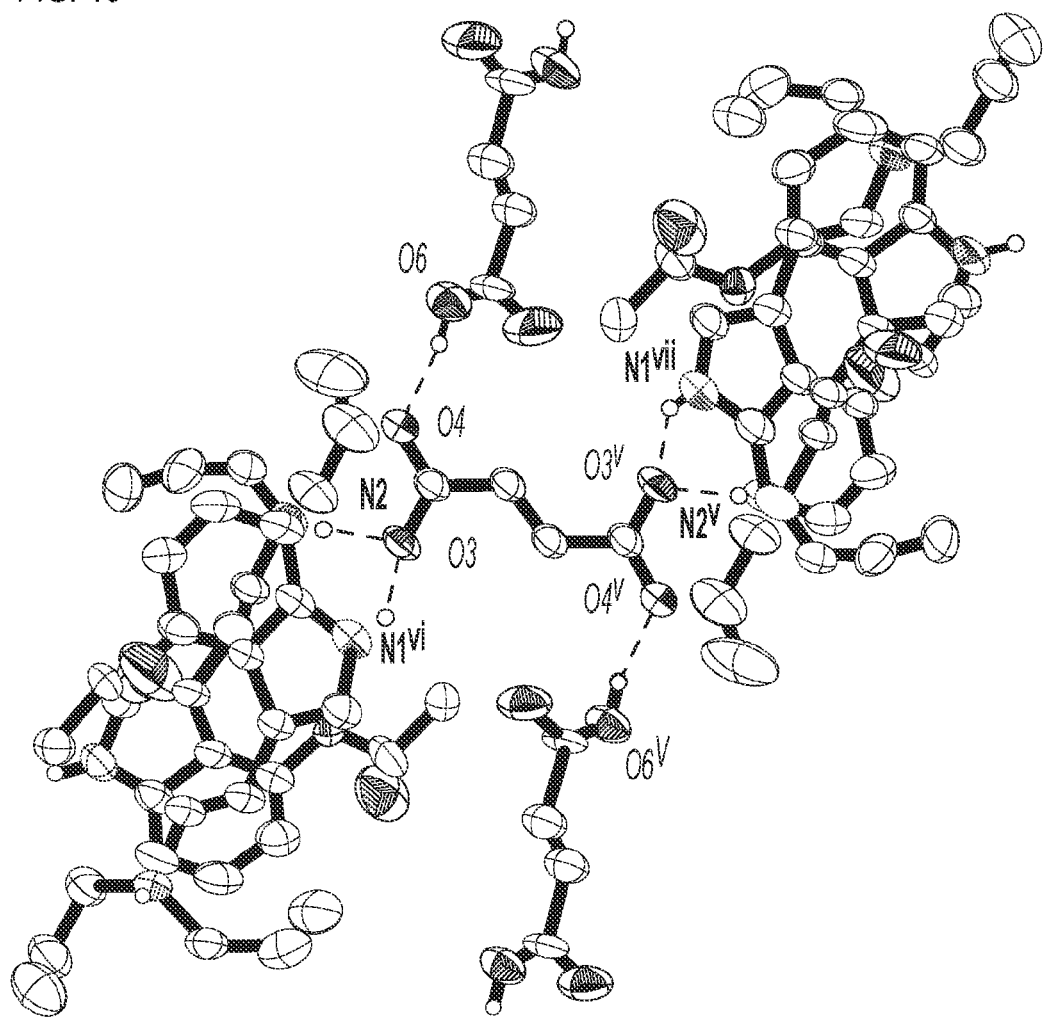
FIG. 10 shows the hydrogen bonding of crystalline 4-AcO-DALT fumarate fumaric acid.

In the extended structure of 4-AcO-DALT fumarate fumaric acid, the N,N-diallyltryptammonium cations, fumarate dianions, and fumaric acid molecules are linked together in a three-dimensional framework through N—H···O and O—H···O hydrogen bonds. The O—H of the fumaric acid, the ammonium N—H, and the indole N—H all hydrogen bond to oxygens of the fumarate dianion, as shown in FIG. 10.

Figure 11:
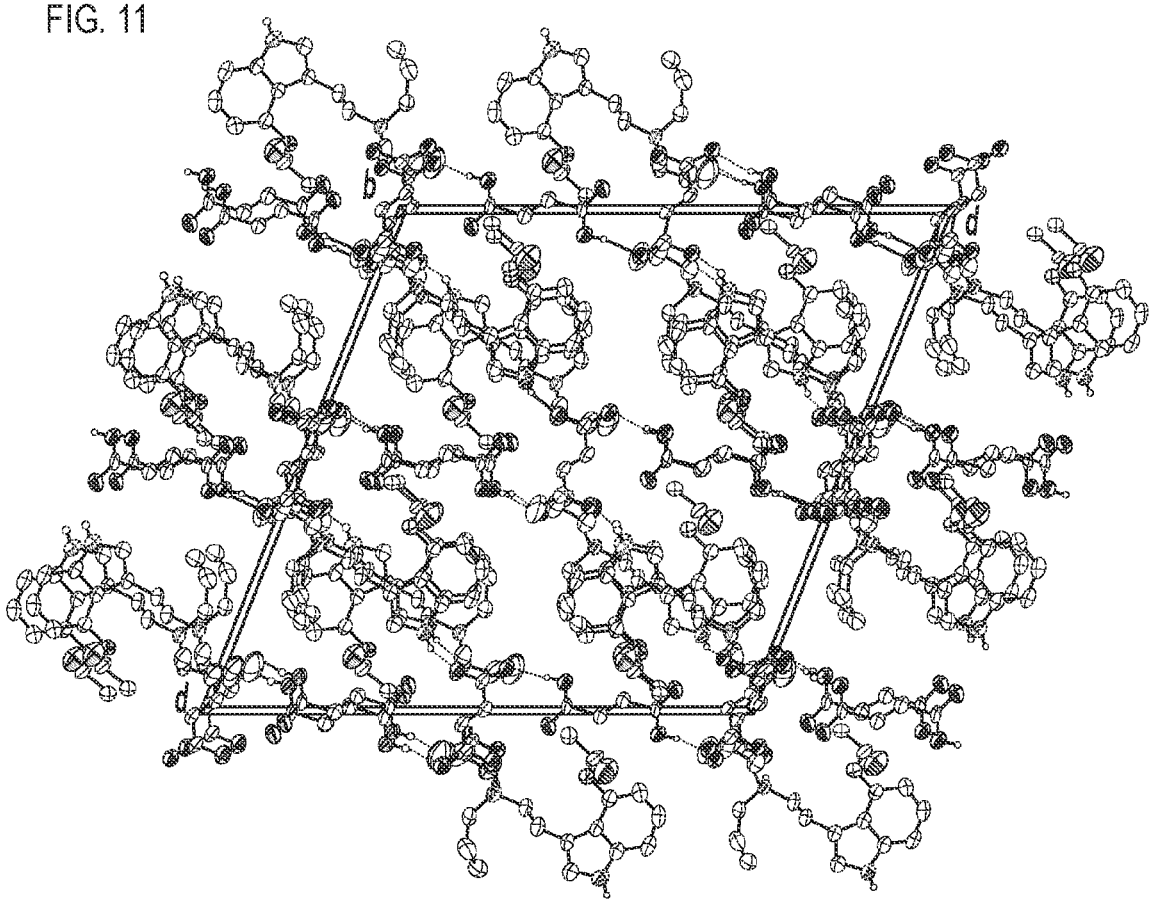
FIG. 11 shows the crystal packing of crystalline 4-AcO-DALT fumarate fumaric acid.

The crystal packing of 4-AcO-DALT fumarate fumaric acid viewed along the b-axis is shown in FIG. 11.

Figure 12:
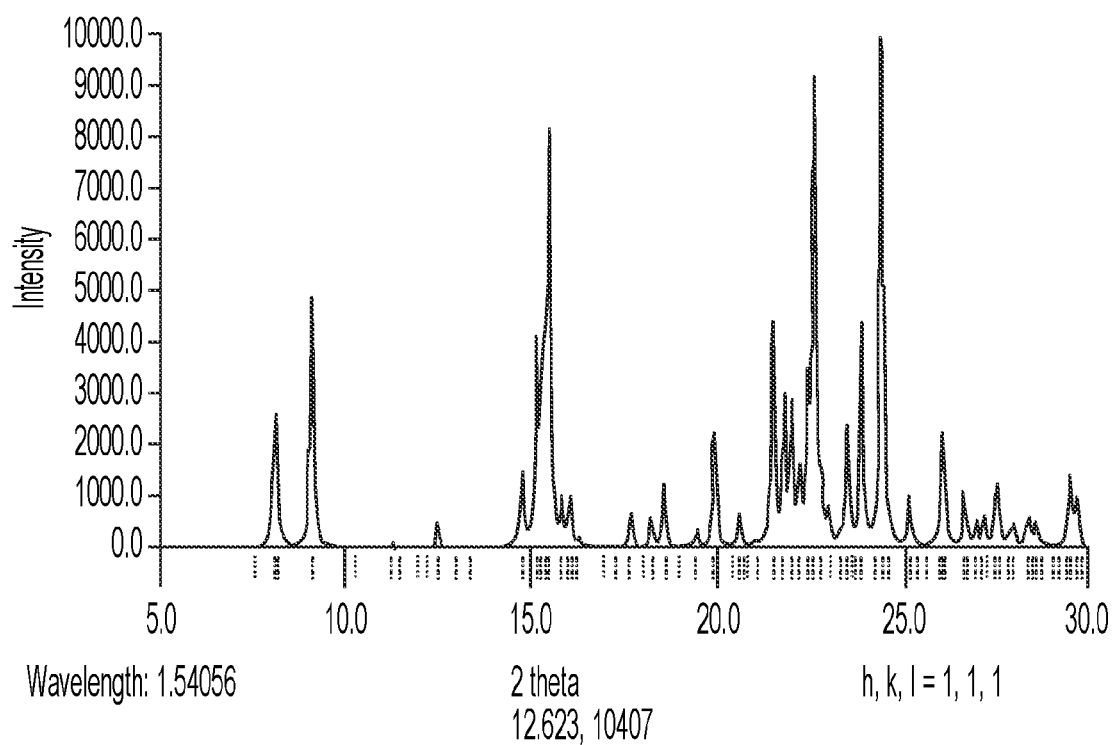
FIG. 12 shows a simulated x-ray power diffraction (XRPD) of crystalline 4-AcO-DALT fumarate fumaric acid.

FIG. 12 is a simulated x-ray powder diffraction (XRPD) of crystalline 4-AcO-DALT fumarate fumaric acid from its single crystal data. Crystalline 4-AcO-DALT fumarate fumaric acid may be characterized by the XRPD peaks at 9.1, 14.7, and 19.9°2θ±0.2°2θ as well as by an XRPD pattern substantially similar to FIG. 12.

REFERENCES

Bruker (2018). APEX3, SAINT, and SADABS. Bruker AXS Inc., Madison, Wis., USA.
Byock, I. (2018). J. Palliat. Med. 21, 417-421.
Daniel, J. & Haberman, M. (2017). Mental Health Clinician, 7, 24-28.
Dolomanov, O. V., Bourhis, L. J., Gildea, R. J., Howard, J. A. K. & Puschmann, H. (2009). J. Appl. Cryst. 42, 339-341.
Feltman, R. (2019). Popular Science. https://popsci.com/story/health/psilocybin-magic-mushroom-fda-break-throughdepression/
Geiger, H. A., Wurst, M. G. & Daniels, R. N. (2018). ACS Chem. Neurosci. 9, 2438-2447.
Lehmann, S., Kieliba, T., Beike, J., Thevis, M. & Mercer-Chalmers-Bender, K. (2017).J. Chromatogr. B 1064, 124-138.
Nichols, D. E. & Frescas, S. (1999). Synthesis, pp. 935-938.
Sheldrick, G. M. (2015a). Acta Cryst. A71, 3-8.
Sheldrick, G. M. (2015b). Acta Cryst. C71, 3-8.
Westrip, S. P. (2010). J. Appl. Cryst. 43, 920-925.

The claimed invention is:

1. A crystalline psilacetin derivative selected from the group consisting of crystalline 4-acetoxy-N-methyl-N-ethyltryptammonium (4-AcO-MET) hydrofumarate, crystalline 4-acetoxy-N-methyl-N-allyltryptammonium (4-AcO-MALT) hydrofumarate, and crystalline 4-acetoxy-N,N-diallyltryptammonium (4-AcO-DALT) fumarate fumaric acid.

2. A composition comprising a crystalline psilacetin derivative according to claim 1 and an excipient.

3. A composition comprising a crystalline psilacetin derivative according to claim 1 and a second component selected from (a) a serotonergic drug, (b) a purified psilocybin derivative, (c) one or two purified cannabinoids and (d) a purified terpene.

4. A method of treating a psychological disorder comprising the step of:
   administering to a subject in need thereof a therapeutically effective amount of a crystalline psilacetin derivative according to claim 1.

5. A method of treating a psychological disorder comprising the step of:
   administering to a subject in need thereof a composition according to claim 2.

6. A method of treating inflammation and/or pain comprising the step of:
   administering to a subject in need thereof a therapeutically effective amount of a crystalline psilacetin derivative according to claim 1.

7. A method of treating inflammation and/or pain comprising the step of:
   administering to a subject in need thereof a composition according to claim 2.

8. A method of treating a psychological disorder comprising the step of:
   administering to a subject in need thereof a composition according to claim 3.

9. A method of treating inflammation and/or pain comprising the step of:
   administering to a subject in need thereof a composition according to claim 3.

10. A composition of claim 2 wherein the crystalline psilacetin derivative is crystalline 4-acetoxy-N-methyl-N-ethyltryptammonium (4-AcO-MET) hydrofumarate.

11. A composition of claim 2 wherein the crystalline psilacetin derivative is crystalline 4-acetoxy-N-methyl-N-allyltryptammonium (4-AcO-MALT) hydrofumarate.

12. A composition of claim 2 wherein the crystalline psilacetin derivative is crystalline 4-acetoxy-N,N-diallyltryptammonium (4-AcO-DALT) fumarate fumaric acid.

13. A composition of claim 3 wherein the crystalline psilacetin derivative is crystalline 4-acetoxy-N-methyl-N-ethyltryptammonium (4-AcO-MET) hydrofumarate.

14. A composition of claim 3 wherein the crystalline psilacetin derivative is crystalline 4-acetoxy-N-methyl-N-allyltryptammonium (4-AcO-MALT) hydrofumarate.

15. A composition of claim 3 wherein the crystalline psilacetin derivative is crystalline 4-acetoxy-N,N-diallyltryptammonium (4-AcO-DALT) fumarate fumaric acid.

16. A crystalline psilacetin derivative of claim 1 wherein the crystalline psilacetin derivative is crystalline 4-acetoxy-N-methyl-N-ethyltryptammonium (4-AcO-MET) hydrofumarate characterized by:

a monoclinic, $P2_1$ crystal system space group at a temperature of about 200 K, unit cell dimensions a=7.9555 (4) Å, b=13.3696 (7) Å, c=9.9708 (5) Å, and β=112.874 (2)°, an XRPD having peaks at 11.7, 16.4, and 20.4°2θ±0.2°2θ, or an XRPD pattern substantially similar to FIG. 4.

17. A crystalline psilacetin derivative of claim 1 wherein the crystalline psilacetin derivative is crystalline 4-acetoxy-N-methyl-N-allyltryptammonium (4-AcO-MALT) hydrofumarate characterized by:

a monoclinic, $P2_1$ crystal system space group at a temperature of about 297 K, unit cell dimensions a=7.9702 (4) Å, b=14.1788 (7) Å, c=9.8035 (5) Å, and β=113.394 (2)°, an XRPD having peaks at 11.6, 15.9, and 17.5°2θ±0.2°2θ, or an XRPD pattern substantially similar to FIG. 8.

18. A crystalline psilacetin derivative of claim 1 wherein the crystalline psilacetin derivative is crystalline 4-acetoxy-N,N-diallyltryptammonium (4-AcO-DALT) fumarate fumaric acid characterized by:

a monoclinic, P2/c crystal system space group at a temperature of about 297 K, unit cell dimensions a=23.6642 (19) Å, b=8.4204 (18) Å, c=23.4002 (18) Å, and β=111.614 (6)°, an XRPD having peaks at 9.1, 14.7, and 19.9°2θ±0.2°2θ, or an XRPD pattern substantially similar to FIG. 12.

* * * * *